United States Patent [19]
Hamula

[11] Patent Number: 5,338,191
[45] Date of Patent: Aug. 16, 1994

[54] ORTHODONTIC BAND WITH ANTITIP REST AND DRIVING NOTCH

[76] Inventor: Warren Hamula, 1539 S. Eighth St., Colorado Springs, Colo. 80906

[21] Appl. No.: 125,155

[22] Filed: Sep. 23, 1993

[51] Int. Cl.⁵ ............................................. A61C 3/00
[52] U.S. Cl. ................................................ 433/23
[58] Field of Search .................................... 433/23

[56] References Cited

U.S. PATENT DOCUMENTS

| | | | |
|---|---|---|---|
| 1,884,128 | 10/1932 | Myerson | 433/23 |
| 3,513,545 | 5/1970 | Miller | 433/23 |
| 3,990,151 | 11/1976 | Kesling | 433/23 |
| 4,192,068 | 3/1980 | Wolfson | 433/23 |

OTHER PUBLICATIONS

"Rocky Mountain Metal Products" catalog, 1954, pp. 3 and 22.

*Primary Examiner*—John J. Wilson
*Attorney, Agent, or Firm*—Fields, Lewis, Pittenger, Rost & Smith

[57] ABSTRACT

In accordance with the present invention, an improvement is provided in an annular orthodontic band for encircling the crown of a molar or bicuspid tooth wherein an antitip rest extends inwardly from a location along the mesial portion of the occlusal edge for a distance which is sufficient for the rest to be engageable with the occlusal surface of the tooth to prevent the mesial side of the band from sliding past the mesial ridge of the tooth. Additional antitip rests can be provided along the occlusal edge of one or more of the buccal, lingual and distal portions of the band for additional bodily support for proper positioning of the band. A ledge can be provided on the band for engagement by an instrument to seat the band on the tooth. A ball hook can be positioned on the gingival side of the ledge of a band for an upper tooth.

16 Claims, 2 Drawing Sheets

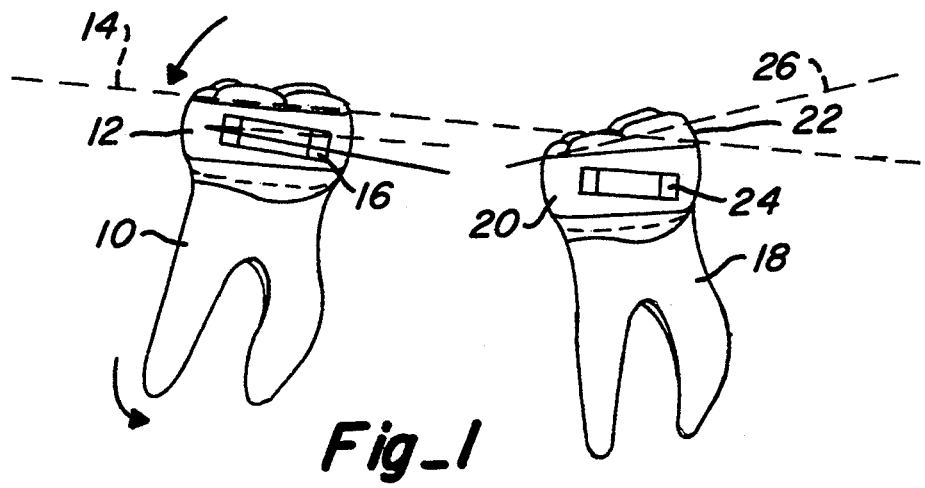
Fig_1
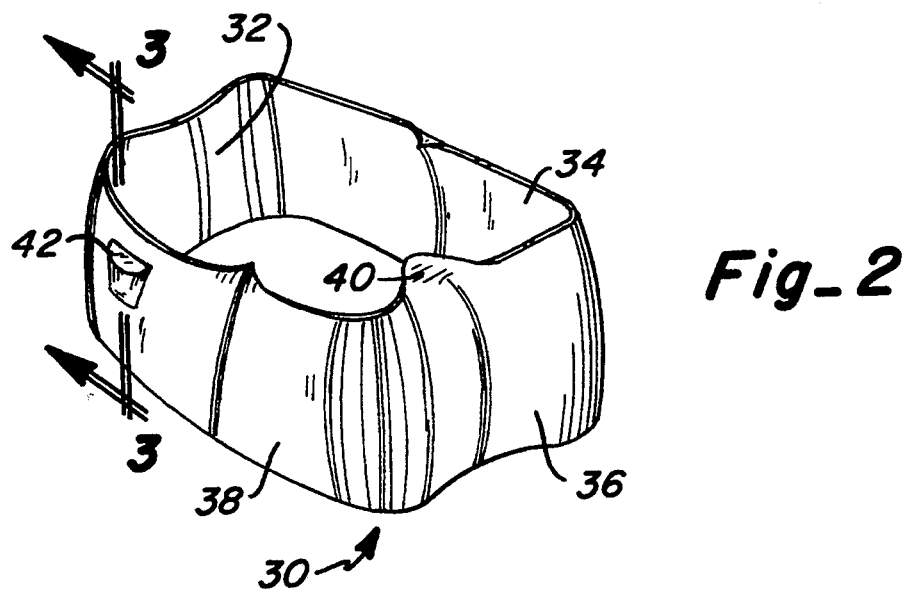
Fig_2
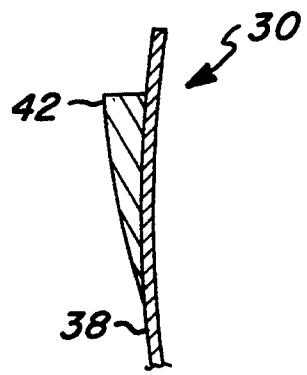
Fig_3

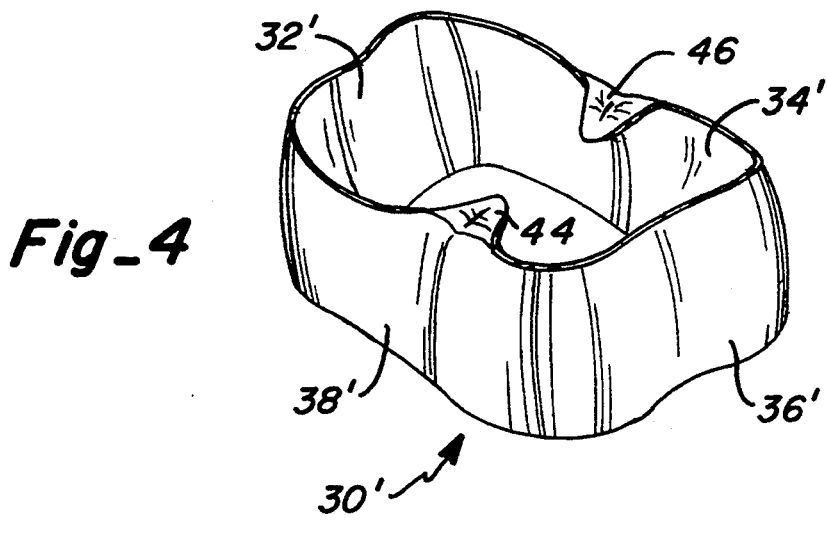
Fig_4
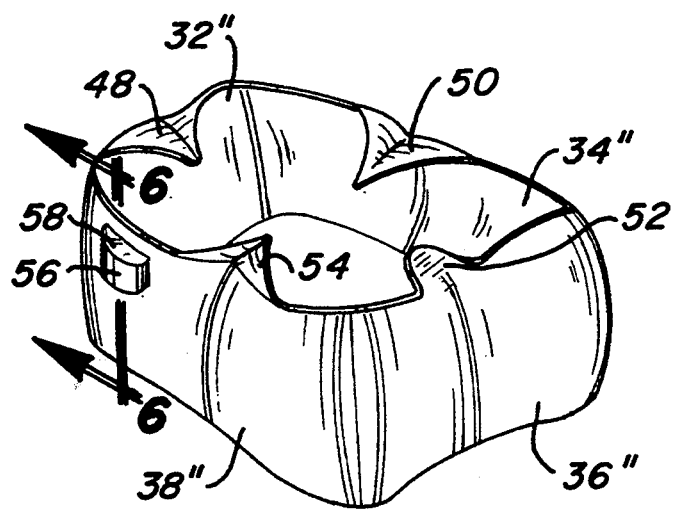
Fig_5
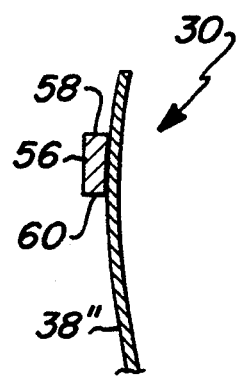
Fig_6
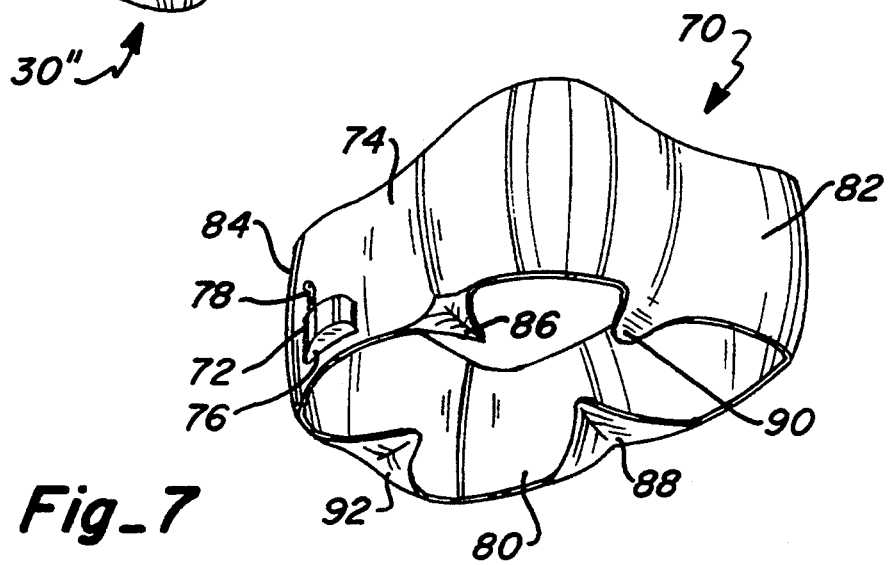
Fig_7

ORTHODONTIC BAND WITH ANTITIP REST AND DRIVING NOTCH

TECHNICAL FIELD

This invention relates to an orthodontic band and more particularly to a band having an antitip rest to prevent the mesial side of the band from slipping below the crown.

BACKGROUND ART

The field of orthodontics is a highly developed one which continues to seek improvements as better materials and techniques become available. Because of the increased cost of medical services, it becomes more important that the orthodontic bands be provided which can be applied to the patient's teeth by technicians without the assistance of the doctor. However, for this to be done, the appliances must be made in such a way that they are simply and correctly applied. A common problem with bands now available is that they are commonly misfitted on molars and bicuspid teeth wherein the band tips beyond the mesial ridge of the tooth. The band is stopped from moving downward on the mesial side because it wedges at the mesial contact point or stops because of mesial tissue resistance. If this misalignment of the band goes undetected by the doctor or staff, it eventually causes mechanical problems that can only be corrected by rebanding, which results in the loss of treatment time. In addition, two major problems are created. First, the roots of the tooth are kicked forward mesially in the alveolar bone crypt. Also, the mesial marginal ridge and crown is forced too far above the normal occlusal plane unfavorably affecting occlusion. The over eruption of the molar then can cause opening of the bite and premature contacts during treatment. This can create major problems in open-bite cases which are hard enough to treat when bands are properly placed.

Additionally, the great use of pre-welded attachments makes exact placement of the bands even more critical. This is true, because the welded attachments are attached to the band in a position which assumes that the band will be properly installed on the tooth. However, if the mesial side of the band slides downwardly beyond the crown, the welded attachments will be at an improper angle thereby adding to the difficulty in properly correcting tooth alignment. In order to provide proper band alignment, various band constructions have been developed, such as those shown in Myerson U.S. Pat. No. 1,884,128 and Kesling U.S. Pat. No. 3,990,151. Each of these bands are suitable for their intended purpose, they require a skilled doctor to install them properly.

Preformed bands such as that shown in Miller U.S. Pat. No. 3,513,545 is intended to provide a better fit. It has portions along the distal and mesial side which are thinner in cross-section and it is contoured to proximate the shape of a molar with the intent of obtaining a better fit.

Wolfson U.S. Pat. No. 4,192,068 discloses a band with a plurality of rests spaced around its perimeter for use with a tool for positioning the band on a tooth.

Although the prior art devices have experienced some success, they each require the skill of the doctor for installation and none of them recognize the requirement of the anatomy of a molar and bicuspid which results in the problem of the mesial side of the band sliding down too far toward the gingival tissue. The anatomy of the tooth which creates this problem is the fact that the distal side of the crown has a curved or bulbus shape whereas the mesial side of the crown is straighter. Thus, when a band is placed over the tooth, the distal side of the crown of the tooth because of its shape generally prevents the band from sliding too far down. However, since the mesial side has a straighter configuration, there is nothing to prohibit the band from moving down until it becomes wedged on the crown or is stopped by engagement with the gingival tissue. This can cause undesirable forces to be applied to a molar or bicuspid, adding to the problems of straightening the teeth.

DISCLOSURE OF THE INVENTION

In accordance with the present invention, an improvement is provided in an annular orthodontic band for encircling the crown of a molar or bicuspid tooth wherein an antitip rest extends inwardly from a location along the occlusal edge for a distance which is sufficient for the rest to be engageable with the occlusal surface of the tooth to prevent the mesial side of the band from sliding past the mesial ridge of the tooth. More particularly, the antitip rest can extend inwardly from a location along the mesial portion of the occlusal edge.

In an alternative embodiment, the antitip rest can extend in from one or both of the buccal and lingual portions of the occlusal edge.

In a still further embodiment, an antitip rest could extend inwardly along the distal occlusal edges.

Advantageously, a notch can be formed on the buccal side of the band for use in seating the band on the tooth. The notch or ledge can have a flat occlusal surface for engagement by an instrument for seating the band and a flat gingival surface for engagement by an instrument for removing the band. A glass ionomer cement is a suitable material for attaching the band to the tooth.

Additional advantages of the invention will become apparent, taken in conjunction with the accompanying drawings.

BRIEF DESCRIPTION OF THE DRAWINGS

FIG. 1 is a perspective view showing two molars with bands installed wherein one band is properly installed and the other one has slid down beyond the crown on the mesial side;

FIG. 2 is a perspective view of one form of the orthodontic band of this invention;

FIG. 3 is an enlarged vertical section, taken along line 3—3 of FIG. 2, showing details of a notch for installing the band;

FIG. 4 is a perspective view, similar to FIG. 2, but showing an alternative embodiment;

FIG. 5 is a perspective view, similar to FIGS. 2 and 4, but showing a still further alternative embodiment;

FIG. 6 is an enlarged vertical section, taken along line 6—6 of FIG. 5, showing details of an alternative notch for installing and removing the band; and FIG. 7 is a perspective view of a band for installation on an upper molar, having a ball hook.

BEST MODE FOR CARRYING OUT THE INVENTION

As best shown in FIG. 1, a molar tooth 10 is shown having a properly placed band 12 wherein the occlusal surface of the tooth lies in the desired occlusal plane 14.

Thus, welded attachment 16 which has been preattached to the band at a slight angle, such as 5° to the occlusal plane, can be utilized to rotate the tooth in the direction of the arrows. On the other hand, tooth 18 has a band 20 which has slipped down on the mesial side 22. This resulted in any force put on the tooth by an orthodontic wire (not shown) on attachment 24 causing the roots of the tooth to rotate forwardly so that the occlusal plane 26 of the tooth now is misaligned with the intended occlusal plane 14.

A band 30 is shown in FIG. 2 which is constructed in accordance with a preferred form of this invention. This band has a distal side 32, a lingual side 34, a mesial side 36 and buccal side 38. Conveniently, an antitip rest 40 is formed at the occlusal edge of mesial side 36. This rest extends inwardly a sufficient distance so as to be engageable with the occlusal portion of the tooth when the band is in place and prevents the mesial side 36 of the band from moving beyond the crown of the tooth. Conveniently, a notch 42 can be formed in the buccal side 38 in a disto-buccal position, as clearly shown in FIGS. 2 and 3. This can be used to set the band on the tooth by means of an appropriate instrument, as is well-known in the art.

An alternative embodiment is shown in FIG. 4 wherein a band 30' is provided with a distal side 32', a lingual 34', a mesial side 36' and a buccal side 38'. In this embodiment, an antitip rest 44 is provided on the occlusal edge of buccal side 38' and second antitip rest 46 is provided on the occlusal edge of lingual side 34'. These antitip rests each extend inwardly a sufficient distance so as to be engageable with the occlusal surface of the tooth on which the band is placed to prevent the mesial side 36' from sliding down beyond the crown of the tooth. They also give more bodily support for proper positioning of the band.

A still further embodiment is shown in FIG. 5 wherein a band 30" has a distal side 32", a lingual side 34", a mesial side 36" and a buccal side 38". The distal side 32" has an antitip rest 48 extending inwardly from the occlusal edge thereof. The lingual side 34" has an antitip rest 50 extending inwardly from the occlusal edge thereof, while mesial side 36" has an antitip rest 52 extending inwardly from the occlusal side thereof. Finally, the buccal side 38" has an antitip reset 54 extending inwardly from the occlusal edge thereof. Each of these antitip resets extend in a sufficient distance so as to be engageable with the occlusal surface of the tooth on which the band is placed to accurately position the band on the tooth so that neither the mesial side 36' nor any other portion of the band slides downwardly beyond its intended position. They also give more bodily support for proper positioning of the band.

Band 30" is also provided with a notch 56 welded thereto which has an upper or occlusal flat surface 58 in engagement with a suitable tool for installing the band on the tooth. Notch 56 can also be provided with a lower or gingival flat surface 60, as best seen in FIG. 6, for engagement with a tool for removing the band after proper orientation of the teeth has been obtained. If desired, additional notches can be provided around the tooth to facilitate installation of the band.

Although the invention has been described for use on the lower molar and bicuspid teeth, it should be understood that the invention can be used on upper molars and bicuspids. In FIG. 7, a band 70 is shown in perspective. In this embodiment, a notch or ledge 72 is attached to the lingual portion 74 of the band and has a rest 76 for seating the band on the tooth. The notch 72 has a ball hook 78 attached to the upper surface thereof, as by welding, for attachment of a rubber band. The band 70 also has a buccal portion 80, a mesial portion 82 and a distal portion 84. Conveniently, one or more rests may be provided along the occlusal edge, such as rest 86 on the occlusal edge of lingual portion 74; rest 88 on the occlusal edge of buccal portion 80; rest 90 on the occlusal edge of mesial portion 82 and rest 92 on the occlusal edge of distal portion 84. As described with the band for the lower molar and bicuspid, the rests will be used in the same manner and serve the same function as previously described. In this regard, in most circumstances only rest 90 will be required to prevent the mesial edge of the band from sliding too far up on the molar. The other rests can be omitted for most applications or if included will further help in positioning the band in its desired location.

From the foregoing, the advantages of this invention can be seen. Several embodiments of bands have been provided having one or more antitip rests which are engageable with an occlusal portion of the tooth to prevent the mesial side of the band from slipping down over the crown into a misaligned position. Also, by means of one or more notches, the band can easily be installed into its proper location. By use of the antitip rest, the work of installing the band can be delegated to a technician in the doctor's office. Furthermore, in the embodiment shown in FIG. 2, since the antitip rest is on the mesial side of the tooth, it is virtually impossible for the technician to place the band on backwards or upside down. Similarly, the other embodiments will prohibit the band from being placed upside down and should help the installer to be sure that the band is properly oriented as well.

This invention has been described in detail with reference to particular embodiments thereof, but it will be understood that various other modifications can be effected within the spirit and scope of this invention.

I claim:

1. An improvement in an annular orthodontic band for encircling the crown of a molar or bicuspid tooth, having buccal, distal, lingual and mesial sides and occlusal and gingival edges, the improvement comprising:
    an antitip rest extending inwardly from a location along said occlusal edge a distance which is sufficient for said rest to be engageable with the occlusal surface of the tooth to prevent said mesial side of said band from sliding past the mesial ridge of the tooth.

2. Apparatus, as claimed in claim 1, wherein:
    said location is along the mesial portion of said occlusal edge.

3. Apparatus, as claimed in claim 1, wherein:
    said location is along at least one of the buccal and lingual portions of said occlusal edge.

4. Apparatus, as claimed in claim 3, wherein:
    said location is along both the buccal and lingual portions of said occlusal edge.

5. Apparatus, as claimed in claim 1, wherein:
    said location is along the distal portion of said occlusal edge.

6. Apparatus, as claimed in claim 1, said improvement further including:
    a ledge formed on one of said buccal and lingual sides of said band for use in seating said band on the tooth.

7. Apparatus, as claimed in claim 6, wherein said ledge includes:
   a flat occlusal surface for installing said band; and
   a flat gingival surface for removing said band.

8. Apparatus, as claimed in claim 7 further including:
   a ball hook welded to said flat gingival surface of said ledge.

9. An orthodontic appliance comprising:
   an annular band for encircling the crown of a molar or bicuspid tooth, having an inner surface, buccal, distal, lingual and mesial sides and occlusal and gingival edges; and
   a first antitip rest extending inwardly from the mesial portion of said occlusal edge a distance which is sufficient for a said first antitip rest to be engageable with the occlusal surface of the tooth to prevent said mesial side of said band from sliding past the mesial ridge of the tooth.

10. Apparatus, as claimed in claim 9, further including:
    a ledge formed on one of the disto-buccal and disto-lingual sides of said band for use in seating said band on the tooth.

11. Apparatus, as claimed in claim 10, wherein said ledge further includes:
    a flat occlusal surface for installing said band; and
    a flat gingival surface for removing said band.

12. Apparatus, as claimed in claim 11 further including:
    a ball hook welded to said flat gingival surface of said ledge.

13. Apparatus, as claimed in claim 9, further including:
    a glass ionomer cement on said inner surface of said band for attaching said band to the tooth.

14. Apparatus, as claimed in claim 9, further including:
    a second antitip rest extending inwardly from at least one of the buccal and lingual portions of said occlusal edge a distance which is sufficient for said second rest to be engageable with the occlusal surface of the tooth to prevent said mesial side of said band from sliding past the mesial ridge of the tooth and to give bodily support for proper positioning of said band.

15. Apparatus, as claimed in claim 14, further including:
    another antitip rest extending inwardly from the distal portion of said occlusal edge a distance which is sufficient for said another rest to be engageable with the occlusal surface of the tooth to prevent said mesial side of said band from sliding past the mesial ridge of the tooth and to give bodily support for proper positioning of said band.

16. An orthodontic appliance comprising:
    an annular band for encircling the crown of a molar or bicuspid tooth, having an inner surface, buccal, distal, lingual and mesial sides and occlusal and gingival edges;
    a first antitip rest extending inwardly from the mesial portion of said occlusal edge a distance which is sufficient for a said first rest to be engageable with the occlusal surface of the tooth to prevent said mesial side of said band from sliding past the mesial ridge of the tooth;
    a second antitip rest extending inwardly from at least one of the buccal and lingual portions of said occlusal edge a distance which is sufficient for said second rest to be engageable with the occlusal surface of the tooth to prevent said mesial side of said band from sliding past the mesial ridge of the tooth; and
    another antitip rest extending inwardly from the distal portion of said occlusal edge a distance which is sufficient for said another rest to be engageable with the occlusal surface of the tooth to prevent said mesial side of said band from sliding past the mesial ridge of the tooth and to give bodily support for proper positioning of said band.

* * * * *